(12) United States Patent
Canfield

(10) Patent No.: US 10,940,221 B2
(45) Date of Patent: Mar. 9, 2021

(54) ULTRASOUND SYSTEM WITH DISINFECTING FEATURE

(71) Applicant: KONINKLIJKE PHILIPS N.V., Eindhoven (NL)

(72) Inventor: Earl M. Canfield, Snohomish, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 2 days.

(21) Appl. No.: 15/756,631

(22) PCT Filed: Aug. 31, 2016

(86) PCT No.: PCT/IB2016/055186
§ 371 (c)(1),
(2) Date: Mar. 1, 2018

(87) PCT Pub. No.: WO2017/042662
PCT Pub. Date: Mar. 16, 2017

(65) Prior Publication Data
US 2018/0250428 A1    Sep. 6, 2018

Related U.S. Application Data

(60) Provisional application No. 62/215,799, filed on Sep. 9, 2015.

(51) Int. Cl.
*A61L 2/10* (2006.01)
*A61L 2/24* (2006.01)
*A61B 8/00* (2006.01)

(52) U.S. Cl.
CPC .............. *A61L 2/10* (2013.01); *A61B 8/4422* (2013.01); *A61B 8/462* (2013.01); *A61L 2/24* (2013.01);
(Continued)

(58) Field of Classification Search
CPC .... A61L 2/10; A61L 2202/24; A61L 2202/16; A61L 2202/14; A61B 8/4422; A61B 8/462
See application file for complete search history.

(56) References Cited

U.S. PATENT DOCUMENTS 8,114,346 B2    2/2012 Hyde et al.
9,833,526 B2 *  12/2017 Agafonov ................. A23L 3/28
(Continued)

FOREIGN PATENT DOCUMENTS

| CN | 201184995 Y | 1/2009 |
|---|---|---|
| CN | 203524686 U | 4/2014 |
| KR | 20090050723 A | 5/2009 |

OTHER PUBLICATIONS

Wikipedia: Screensaver 2012 (Year: 2012).*

*Primary Examiner* — Sean E Conley
*Assistant Examiner* — Brendan A Hensel

(57) ABSTRACT

An ultrasound imaging system (100) including a disinfection system is disclosed. The disinfection system may include one or more ultraviolet light sources (115). The UV light sources may be included in a display (105). The disinfection system may be configured to operate when the display is parallel to a control panel (120) of the ultrasound imaging system. The disinfection system may provide indications of the disinfection status of the ultrasound imaging system.

16 Claims, 8 Drawing Sheets

(52) U.S. Cl.
 CPC ....... *A61L 2202/14* (2013.01); *A61L 2202/16* (2013.01); *A61L 2202/24* (2013.01)

(56) References Cited

U.S. PATENT DOCUMENTS

| | | | |
|---|---|---|---|
| 2007/0195550 A1 | 8/2007 | Tsai | |
| 2008/0234577 A1* | 9/2008 | Murkowski | A61B 8/00 600/437 |
| 2011/0256019 A1* | 10/2011 | Gruen | A61L 2/10 422/24 |
| 2013/0062534 A1* | 3/2013 | Cole | A61L 2/10 250/454.11 |
| 2013/0197364 A1* | 8/2013 | Han | A61B 8/463 600/440 |
| 2014/0183377 A1* | 7/2014 | Bettles | A61L 2/10 250/455.11 |
| 2014/0300581 A1* | 10/2014 | Aurongzeb | G06F 1/1601 345/175 |
| 2016/0000951 A1* | 1/2016 | Kreiner | A61L 2/0047 422/24 |
| 2016/0324996 A1* | 11/2016 | Bilenko | A61L 2/10 |
| 2017/0071573 A1* | 3/2017 | Takahashi | A61B 8/14 |
| 2017/0296686 A1* | 10/2017 | Cole | A61L 2/10 |

\* cited by examiner

ULTRASOUND SYSTEM WITH DISINFECTING FEATURE

This application is the U.S. National Phase application under 35 U.S.C. § 371 of International Application No. PCT/I132016/055186, filed on Aug. 31, 2016, which claims the benefit of Provisional Application Ser. No. 62/215,799 filed Sep. 9, 2015. These applications are hereby incorporated by reference herein.

BACKGROUND

Medical devices are prone to contamination by infectious agents such as viruses and bacteria. Even medical devices that do not come in direct contact with a patient may become contaminated. For example, control panels on medical devices (e.g., ultrasound imaging systems, pulse oximeters, IV pumps) may become contaminated when a technician touches a patient and then touches the control panel. A technician may also contaminate the control panel by transferring infectious agents from other locations (e.g., restroom, cafeteria, other control panel). This may increase the risk of transferring an infectious agent to a patient via the medical device.

Control panels and other portions of medical devices are regularly disinfected to avoid cross-contamination. Disinfecting the medical device may be accomplished by cleansing the medical device with a disinfecting solution. The disinfecting solution may be sprayed on and wiped off or the disinfecting solution may be included in a pre-saturated towel that used to wipe down the medical device. While effective, the disinfecting solution is toxic and can degrade surfaces of the medical device.

SUMMARY

An example ultrasound system according to an embodiment of the disclosure may include a display, a control panel, an ultraviolet (UV) light source coupled to the display, wherein the UV light source may be configured to turn on responsive to a control signal, an articulation system coupled to the display that may be configured to position the display, and a controller coupled to the UV light source and the controller may be configured to provide the control signal to turn on the UV light source responsive to the display being positioned in a disinfect position.

An example method of disinfecting an ultrasound imaging system according to an embodiment of the disclosure may include detecting, with a position sensor, a display is in a disinfect position; providing a control signal to an ultra violet (UV) light source to turn on the UV light source; running a timer for a disinfection cycle time; and providing the control signal to the UV light source to turn off the UV light source responsive to completion of the disinfection cycle time, wherein the control signal may be provided by a controller.

DETAILED DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

Ultrasound imaging systems may be portable units on carts that may be transported to different locations, for example, different exam rooms in a hospital. The ultrasound imaging system may include a control panel for operating the ultrasound imaging system and a display for viewing images acquired with the ultrasound imaging system. The display may be a flat panel display that may be moved into different positions. After completing an exam, a sonographer may move the display into a position parallel to the control panel. The display may include one or more ultraviolet (UV) light sources that may power on when the display is in the parallel position. The UV light sources may disinfect the control panel and/or other components of the ultrasound imaging system. As known, UV light may be an effective disinfectant by killing organisms such as bacteria and viruses. After disinfection, the sonographer may return the display to a position viewable to the sonographer and conduct another exam. The disinfection of the control panel may reduce or eliminate cross-contamination between exams.

Figure 1:
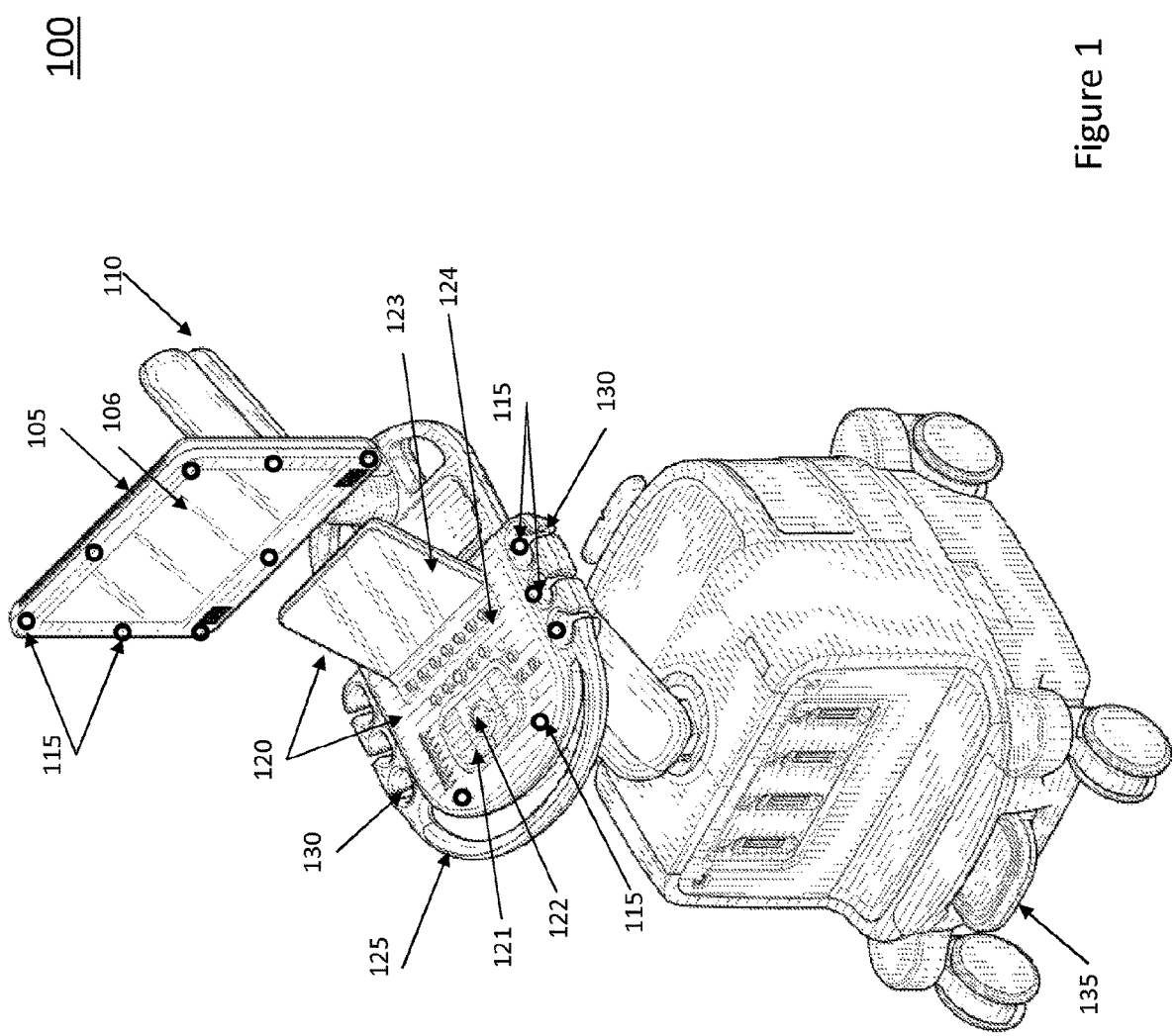
FIG. 1 is a schematic illustration of an ultrasound system including a disinfection system according to an embodiment of the disclosure.

FIG. 1 is a schematic diagram of an ultrasound imaging system 100 including a disinfection system according to at least one embodiment of the disclosure. An ultrasound imaging system may include a display 105 that may be positioned by a user. In some embodiments, the display 105 may be a flat panel display. The display 105 may be articulated to be viewed over a wide range of viewing positions. The articulation may be provided by a two-arm articulation system 110 with a counter-weight assisted 4-bar linkage. The display 105 may have a peripheral gripping surface which may facilitate holding the display 105 and being repositioned with one hand. An example of an ultrasound system having an articulated flat panel display that may be used to implement one or more embodiments of the disclosure may be found in European Patent EP 1713396. The display 105 may be positioned parallel to a control panel 120 of the ultrasound imaging system. The parallel position may facilitate moving the ultrasound imaging system between locations and/or facilitate disinfecting the control panel 120 as will be described further below. The control panel 120 may include one or more control elements for controlling the ultrasound imaging system 100. In the embodiment shown in FIG. 1, the control panel 120 includes a keyboard 121, a track ball 122, control knobs and switches 124, and a flat panel touch screen 123. Other embodiments of the control panel 120 may include more or fewer control elements. Other embodiments of the control panel 120 may include different elements than those shown in FIG. 1. For example, the control panel 120 may include a track pad, one or more rocker switches, and/or microphone.

The display 105 may include one or more UV light sources 115. The UV light sources 115 may be located along a perimeter of a screen portion 106 of display 105, for example, as shown in the embodiment of FIG. 1. In some embodiments, the UV light sources 115 may be embedded within and/or behind the screen portion 106. Examples of UV light sources 115 may include but are not limited to LEDs, pulsed xenon lamps, and fluorescent bulbs. The display 105 may include one or more types of UV light sources 115. The UV light sources 115 may emit UV waves in the range of approximately 100-280 nm, 200 nm-320 nm, 100-320 nm, 250-260 nm, and/or other range suitable for killing organisms such as bacteria and viruses. In some embodiments, the UV light sources 115 may produce UV light having a fluence of 2,000-10,000 µW s/cm².

Figure 2:
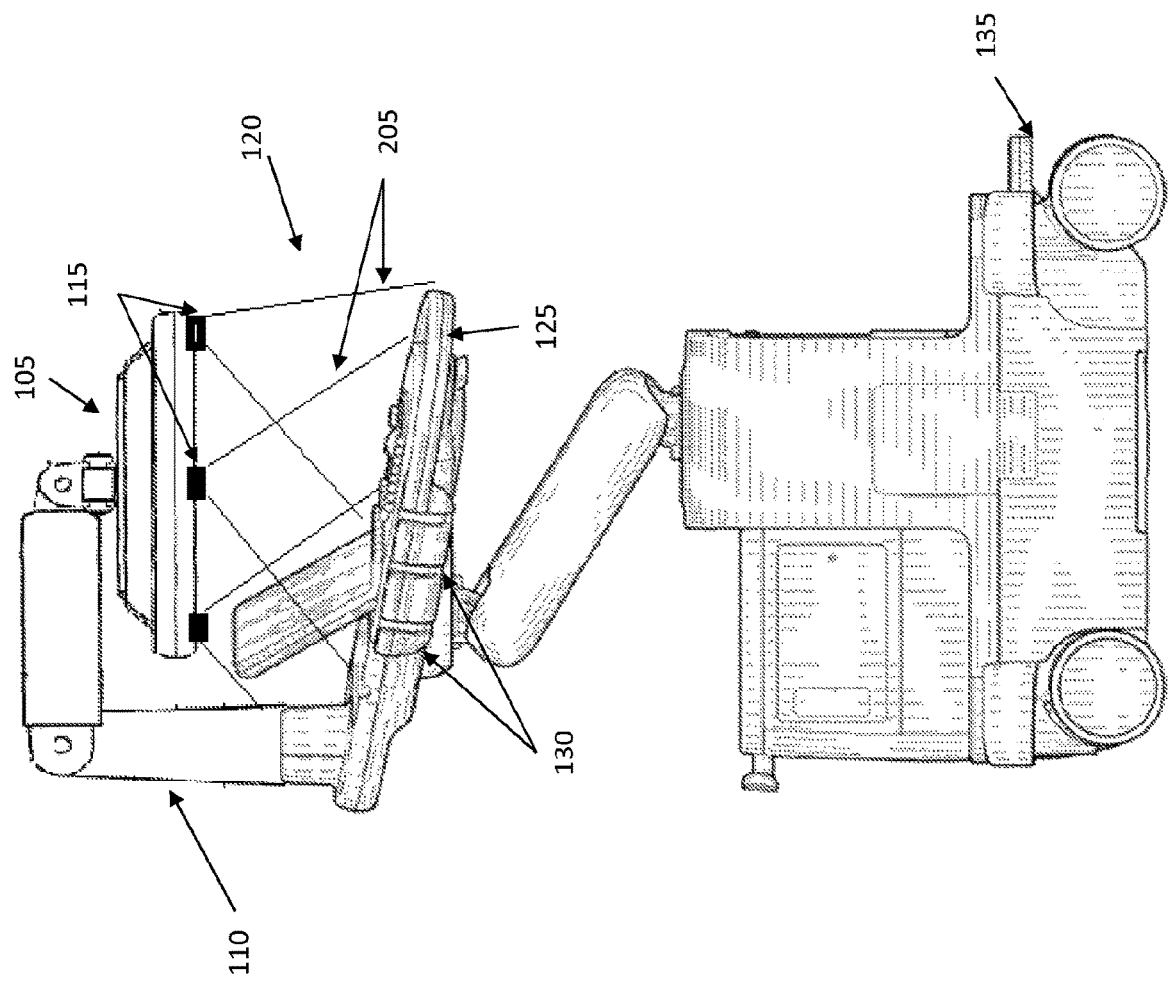
FIG. 2 is a schematic illustration of the ultrasound system including the disinfection system shown in FIG. 1.

FIG. 2 is a schematic diagram of the ultrasound imaging system 100 according to at least one embodiment of the disclosure where the display 105 is in a position parallel to the control panel 120. When the display 105 is in a position parallel to a control panel 120, the UV light sources 115 may illuminate the control panel 120 when powered on. The UV illumination is depicted by lines 205. The UV illumination may disinfect surfaces of the control panel 120 exposed to the UV illumination, including the control elements such as the keyboard 121, track ball 122, control knobs and switches 124, and touch screen 123. In some embodiments, the UV illumination may illuminate other portions of the ultrasound imaging system 100 for disinfection. For example, the UV illumination may disinfect a handle 125, ultrasound probes (not shown), instrument holders 130, ultrasound probe cables (not shown), cable holders (not shown), pedals 135, and/or a combination thereof.

Referring to both FIGS. 1 and 2, in some embodiments, the ultrasound imaging system 100 may include UV light sources 115 other than the display 105. For example, UV light sources 115 may be included in instrument holders 130 of the ultrasound imaging system. The UV light sources may illuminate and disinfect the holder 130 and/or at least a portion of an instrument (e.g., handle of an ultrasound probe) in the instrument holder 130. In another example, the UV light sources 115 may be included under a keyboard 121 of the control panel 120 (not visible in FIGS. 1 and 2). The UV light sources 115 may illuminate the underside of a track ball 122 of the control panel 120. This may facilitate disinfecting all surfaces of the track ball 122. In another example, the UV light sources 115 may be included in the control panel 120 and/or a periphery of the control panel 120. Theses UV light sources may illuminate the display 105 for disinfection.

Figure 3:
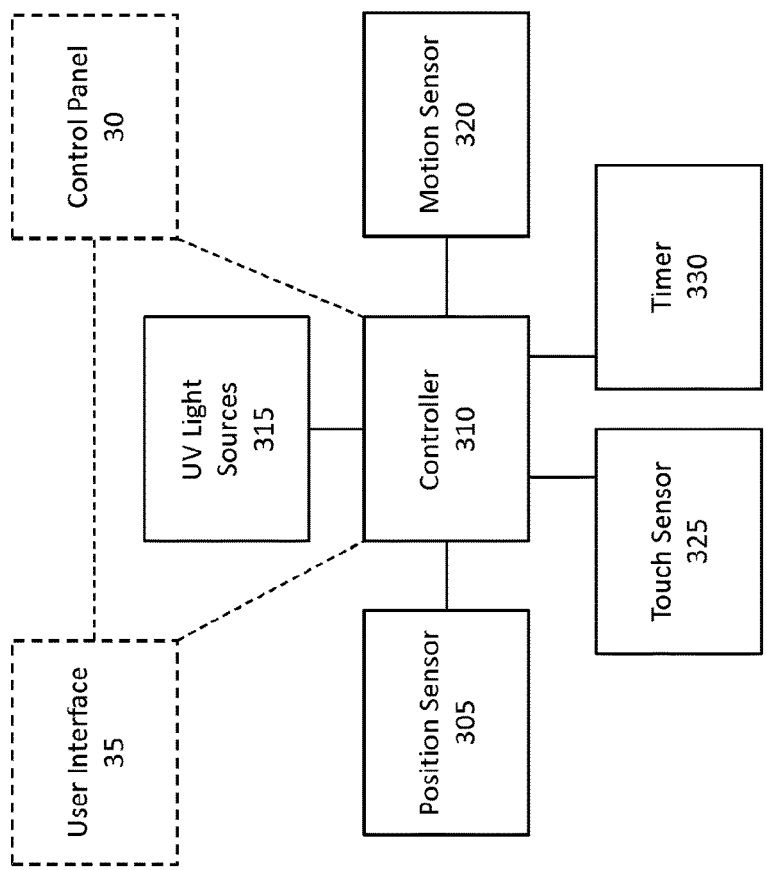
FIG. 3 is a functional block diagram of a disinfection system according to an embodiment of the disclosure.

FIG. 3 is a functional block diagram of a disinfection system 300 of an ultrasound imaging system, such as ultrasound imaging system 100, according to at least one embodiment of the disclosure. The disinfection system 300 may include a position sensor 305 that may detect a position of a display. In some embodiments, the position sensor 305 may be located in an articulation system of the display. The position sensor 305 may provide information on the detected position to a controller 310 of the ultrasound imaging system. The controller 310 may be implemented as hardware, software, or combinations thereof. For example, in some embodiments, the controller 310 may be an integrated circuit including circuits such as logic circuits and computational circuits. The circuits of the controller 310 may operate to execute various operations and provide control signals to other circuits of the disinfection system 300. In some embodiments, the controller 310 may be implemented as multiple controllers. The controller 310 may control the operation of the UV light sources 315. The controller 310 may provide one or more control signals to the UV light sources 315. The UV light sources 315 may turn on and/or off responsive to the one or more control signals. For example, the controller 310 may prevent UV light sources 315 from being powered on and/or the controller 310 may shut off the UV light sources 315 when the display is not in a position parallel to a control panel. This may prevent the UV light sources 315 from being powered on when the display is in an upright position, which may inadvertently illuminate eyes and/or skin of a user and/or patient causing irritation or annoyance. The UV light sources 315 may be implemented as UV light sources 115 in some embodiments.

The UV light sources 315 may illuminate a control panel and/or other portions of the ultrasound imaging system for a period of time to disinfect the surfaces illuminated by the UV light sources 315. The period of time may be several seconds, half a minute, a minute, several minutes, fifteen minutes, an hour, or several hours. In an example embodiment, the period of time is two minutes. The UV light sources 315 may power down after the period of time has elapsed. This period of time may be referred to as a disinfection cycle. The length of the disinfection cycle may be set by a timer 330. The timer 330 may send time information to the controller 310. The controller 310 may be configured to turn off the UV light source 315 when the timer 330 indicates that the disinfection cycle has elapsed. In some embodiments, the timer 330 is pre-programmed. In some embodiments, the timer 330 may be set by a user.

The disinfection system 300 may include a motion sensor 320 and/or touch sensor 325 that may detect when a user's hand has touched the control panel and/or moved between the control panel and the display. The motion sensor 320 and/or touch sensor 325 may provide information on the detected motion and/or touch to the controller 310. The controller 310 may prevent the UV light sources 315 from being powered on and/or shut off the UV light sources 315 when motion and/or touch is detected. This may prevent the UV light sources from being powered on when they may illuminate the skin of a user and/or patient. It may also prevent the ultrasound imaging system from indicating it is disinfected. For example, if a user touches a button of the control panel half-way through a disinfection cycle of the UV light sources 315, the user may contaminate the button.

However, the UV light sources 315 may not illuminate the button for a long enough period of time after the user's touch to fully disinfect the button.

The motion sensor 320 may be included on the display and/or the control panel of the ultrasound imaging system. In an example embodiment, an infrared (IR) light source may be included on the display and an IR light detector may be included on the control panel. The IR light source may provide a beam of IR light to the detector. When the IR light detector detects a break in the beam, the IR light detector may register a detected motion. Other configurations and/or types of motion sensors may be used. In an example embodiment, the touch sensor 325 may be included in the control panel of the ultrasound imaging system. The touch sensor 325 may detect actuation of control elements (e.g., buttons, switches, knobs) based, at least in part, on electrical signals generated with the control elements are actuated. The touch sensor 325 may detect changes in resistance across the control panel as a result of a user coming in contact with the control panel. Other types of touch sensors may also be used.

The controller 310 may be pre-programmed and/or may be programmed by a user. For example, the user may adjust the disinfection cycle time via the control panel 30 of the ultrasound imaging system. In some embodiments, the user may set the disinfection system 300 to run a disinfection cycle automatically whenever the display is in a position parallel to the control panel. In other embodiments, the user may set the disinfection system 300 to run a disinfection cycle when display is in a position parallel to the control panel only at certain times (e.g., once an hour, overnight).

The controller 310 may provide information to a user interface 35 (e.g., a screen portion of the display of the ultrasound imaging system). The information may include the length of a disinfection cycle, the time of the last full disinfection cycle, time of an interrupted disinfection cycle, disinfection status, and/or other information.

Figure 4:
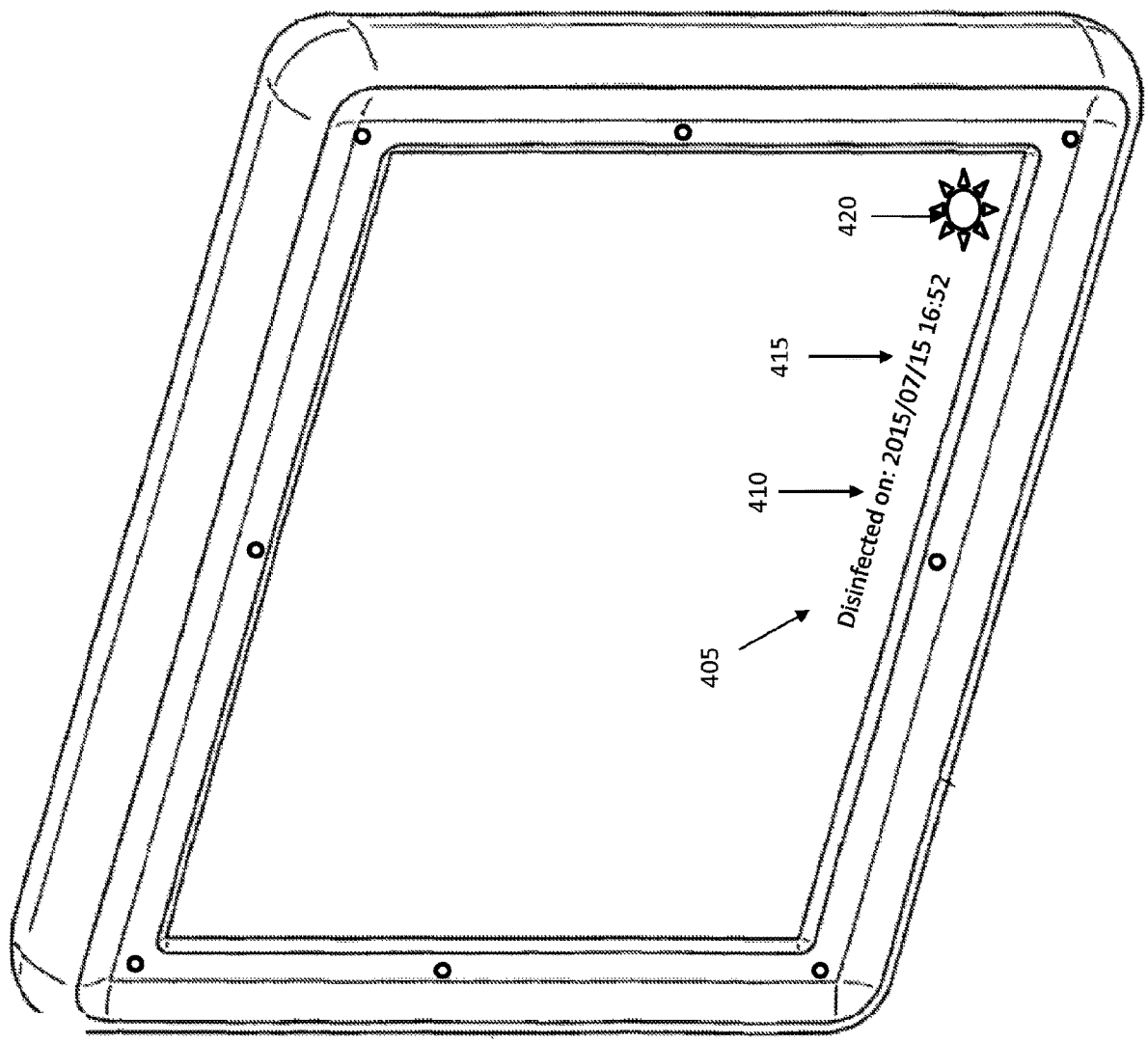
FIG. 4 is an example of a graphical display of a user interface according to an embodiment of the disclosure.
Figure 5:
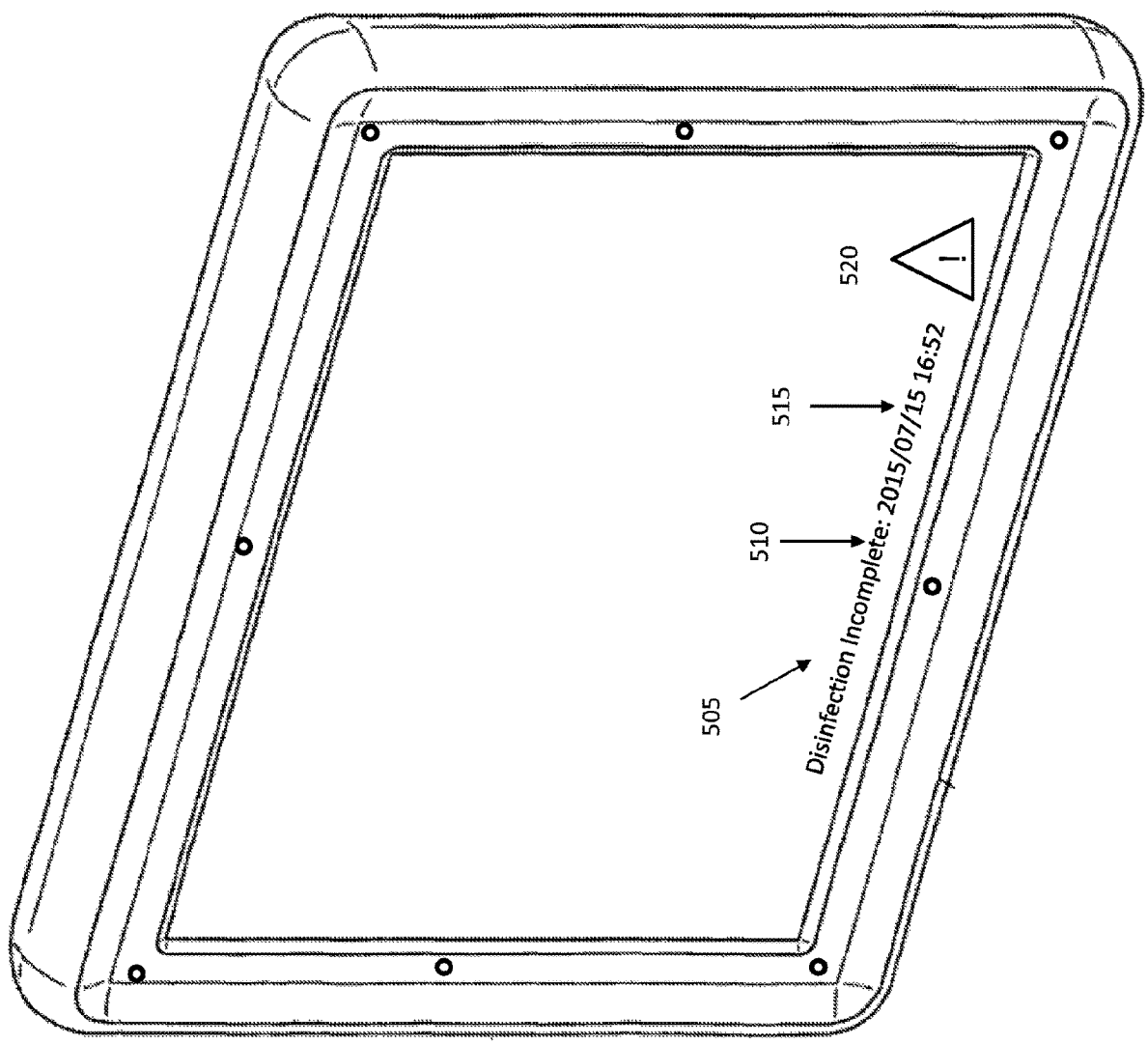
FIG. 5 is an example of a graphical display of a user interface according to an embodiment of the disclosure.
Figure 6:
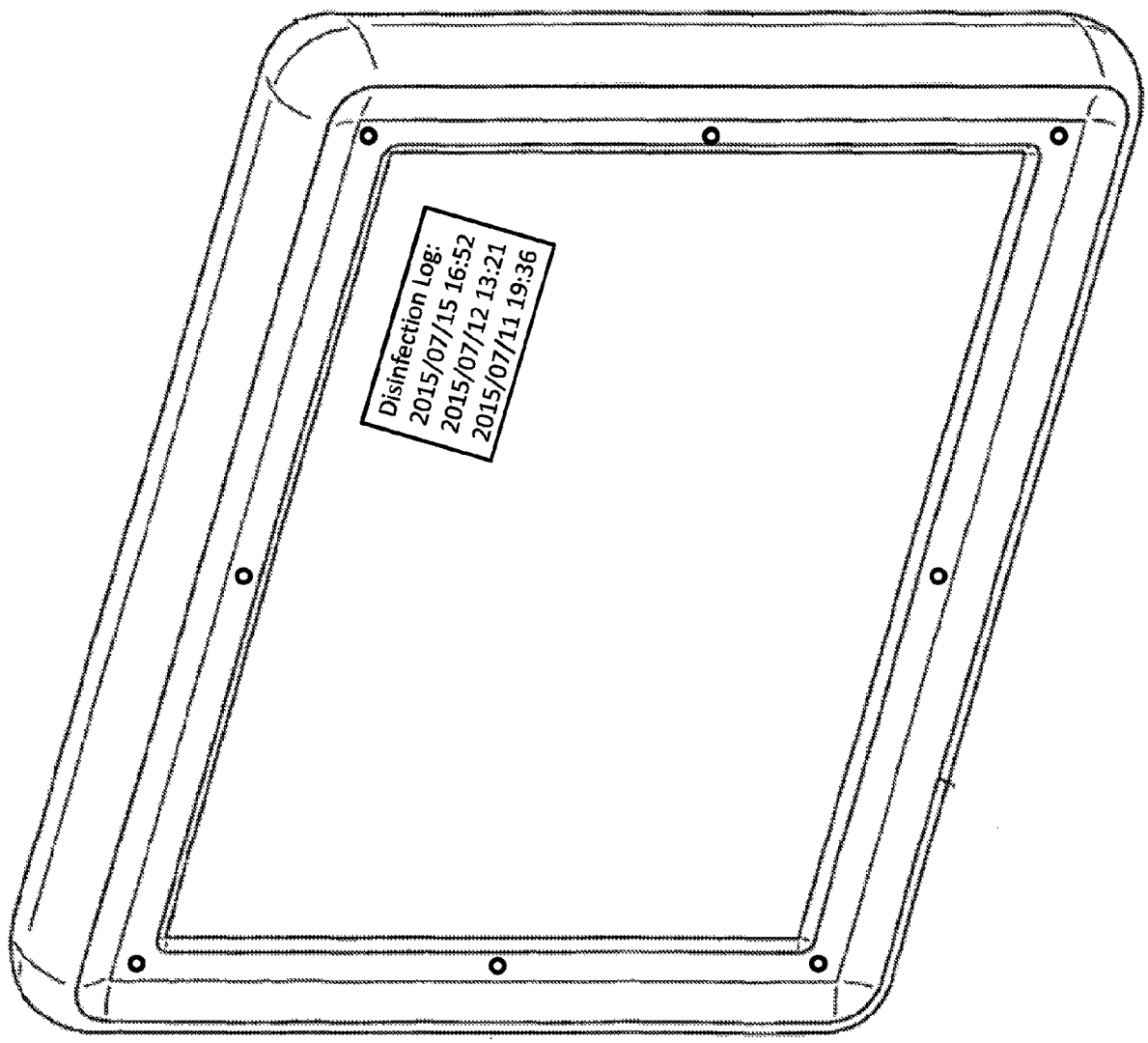
FIG. 6 is an example of a graphical display of a user interface according to an embodiment of the disclosure.

FIGS. 4-6 are schematic illustrations of example graphical displays of a user interface 400 according to at least one embodiment of the disclosure. The user interface 400 may be controlled by hardware, software, or a combination thereof. For example, the user interface 400 may receive information and/or control signals from a controller such as controller 310. In some embodiments, the user interface 400 may receive information and/or control signals from one or more processors of the ultrasound imaging system. The one or more processors may execute software instructions provided on a non-transitory computer readable medium. For example, the processors may generate graphics for the graphical displays and provide the graphics to the user interface 400. The graphical displays of the user interface 400 may be responsive to information received from a controller of a disinfection system, such as controller 310 of disinfection system 300. The graphical displays of the user interface 400 may be shown on a display of an ultrasound imaging system.

FIG. 4 shows an example graphic 405 that indicates that an ultrasound imaging system was successfully disinfected. The graphic 405 may include an icon 420 and text 410 that indicate the system has been disinfected, and/or the time and/or date 415 of the disinfection. The graphic 405 may be helpful to a user to confirm that a disinfection cycle has completed, when the disinfection cycle was completed, and that the system is now considered disinfected. The graphic 405 may be shown on a display of the ultrasound imaging system until a user touches the control panel and/or begins an exam.

FIG. 5 shows an example graphic 505 that indicates that disinfection of an ultrasound imaging system was interrupted. The graphic 505 may include an icon 520, text 510 that indicates the system has not been disinfected, and/or the time and/or date 515 of the interruption. The graphic 505 may be helpful to a user to appreciate that a disinfection cycle was not completed, and that another disinfection cycle may need to be performed before the system is considered disinfected. The graphic 505 may be shown on a display of the ultrasound imaging system until a user touches the control panel and/or begins an exam.

The graphics 405 and 505 shown in FIGS. 4 and 5 are generally located at the bottom portion of the graphical display of the user interface 400. The graphic 405 may be located in other portions of the graphical display of the user interface 400. For example, in some embodiments, the graphic 405 may be generally located at an upper portion of the graphical display of the user interface 400. In other embodiments, the graphic 405 may be located to either the right portion or the left portion of the graphical display of the user interface 400.

FIG. 6 shows an example graphic 605 that indicates past disinfections, which may provide a disinfection log. The graphic 605 may include the times and dates of past disinfections. The graphic 605 may be helpful to a user to provide a historical understanding of, for example, frequency of disinfection cycles, when the last disinfection cycle was performed, as well as other information related to disinfection of the ultrasound imaging system. In some embodiments, the graphic 605 may include interrupted disinfection cycles in addition to completed disinfection cycles. The graphic 605 may be shown on a display of the ultrasound imaging system until a user touches the control panel and/or begins an exam. In some embodiments, the user may access the graphic 605 through the user interface 400 through the control panel. The graphic 605 shown in FIG. 6 is generally located at the upper-right portion of the graphical display of the user interface 400. The graphic 605 may be located in other portions of the graphical display of the user interface 400. For example, in some embodiments, the graphic 605 may be generally located at an upper-left portion of the graphical display of the user interface 400. In other embodiments, the graphic 605 may be located to either the lower-right portion or the lower-left portion of the graphical display of the user interface 400.

FIGS. 4-6 are provided as exemplary displays of a user interface. Other text, colors, shapes, and/or information may be provided by the user interface 400 without departing from the principles of the disclosure.

Figure 7:
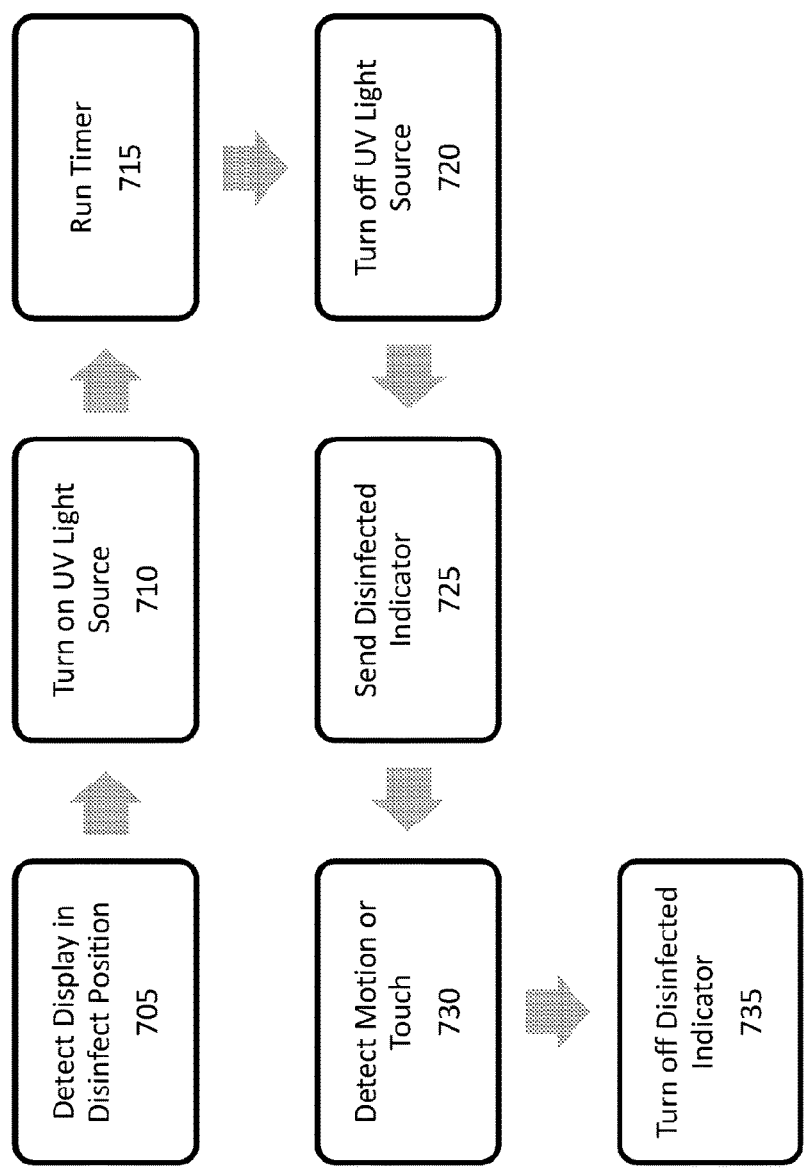
FIG. 7 is a flow chart of a method according to an embodiment of the disclosure.

FIG. 7 is a flow chart of a method 700 according to at least one embodiment of the disclosure. The method 700 may be performed by a disinfection system of an ultrasound imaging system, such as disinfection system 300 of FIG. 3. At Block 705, the disinfection system may detect a display in a disinfect position (e.g., parallel to a control panel). At Block 710, the disinfection system may turn on a UV light source. The disinfection system may then run a timer for a disinfection cycle time at Block 715. In some embodiments, Block 710 and Block 715 may be initiated simultaneously. After the disinfection cycle time has completed, the disinfection system may turn off the UV light source at Block 720. At Block 725, the disinfection system may send a disinfected indicator to a user interface. Responsive to the indicator, the user interface may display a graphic indicating that the ultrasound imaging system has been disinfected. At Block 730, the disinfection system may detect motion of the display, touch on the control panel, and/or portion of the ultrasound imaging system. The disinfection system may then send an indicator to the user interface to stop displaying the graphic indicating that the ultrasound imaging system is disinfected at Block 735.

Figure 8:
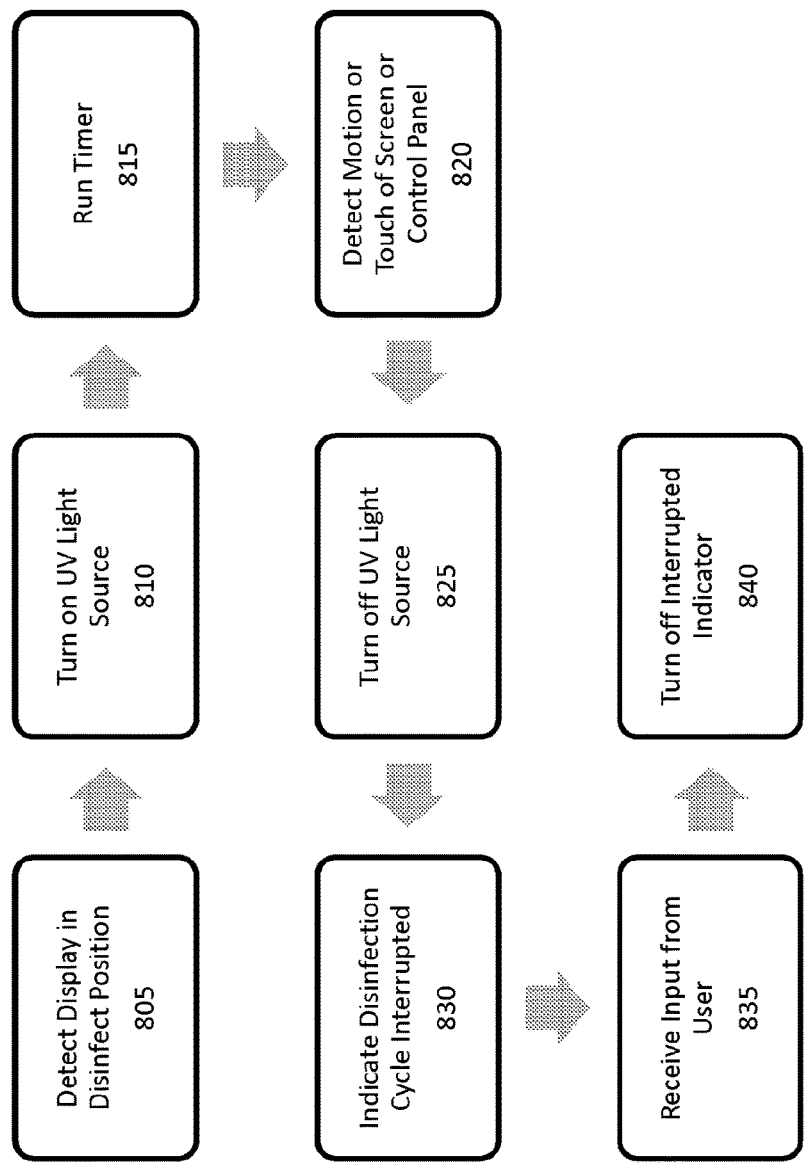
FIG. 8 is a flow chart of a method according to an embodiment of the disclosure.

FIG. 8 is a flow chart of a method 800 according to at least one embodiment of the disclosure. The method 800 may be performed by a disinfection system of an ultrasound imaging system, such as disinfection system 300 of FIG. 3. At Block 805, the disinfection system may detect a display in a disinfect position (e.g., parallel to a control panel). At Block 810, the disinfection system may turn on a UV light source. The disinfection system may then run a timer at Block 815. In some embodiments, Block 810 and Block 815 may be initiated simultaneously. At Block 820, the disinfection system may detect motion of the flat panel display, touch on the control panel, and/or portion of the ultrasound imaging system prior to the end of the timer started at Block 815. The disinfection system may then turn off the UV light source at Block 825 and send an indicator to a user interface that the disinfection cycle was interrupted at Block 830. Responsive to the indicator, the user interface may display a graphic indicating that the ultrasound imaging system has not been disinfected. At Block 835, the disinfection system may detect an input from a user. In some embodiments, the input may be a detected touch on the control panel and/or portion of the ultrasound imaging system. In some embodiments, the input from the user may be an input provided to the user interface to acknowledge viewing the graphic indicating that the ultrasound imaging system has not been disinfected. In some embodiments, the input from the user may be initiating an ultrasound exam. The disinfection system may then send an indicator to the user interface to stop displaying the graphic indicating that the ultrasound imaging system is not disinfected at Block 840. Alternatively, the disinfection system may send an indicator to the user interface to stop displaying the graphic after a set period of time (e.g., five minutes, one hour).

An ultrasound system including a disinfection system may optionally include additional features. For example, a curtain may be coupled to a periphery of a display. The curtain may surround the display and obscure the control panel from view when the display is parallel to the control panel. The curtain may reduce or eliminate UV light from reflecting off the control panel onto other surfaces in a room (e.g., patient eyes and skin, UV sensitive equipment, UV sensitive drugs). In some embodiments, the display may include an indicator on an edge or a back surface. The indicator may indicate a disinfection status of the ultrasound imaging system. For example, an LED may be included on an edge or back surface of the display. The LED may be red during disinfection, green after disinfection, and yellow after an interrupted disinfection cycle. This may allow a user to determine the disinfection status without touching the display. In some embodiments, the ultrasound imaging system may provide audible signals based on the disinfection status. In some embodiments, the ultrasound imaging system may provide disinfection status and/or other information (e.g., disinfection log) to an external computer system. For example, a hospital may have a computer system that tracks the disinfection status of medical devices in the hospital. The information may be transmitted wirelessly, via Ethernet cable, and/or other method.

Although the present system has been described with reference to an ultrasound imaging system, the present system may be extended to other imaging systems and medical devices. Further, the present system may also include one or more elements which may be used with non-ultrasound imaging systems so that they may provide features and advantages of the present system.

Further, the present methods, systems, and apparatuses may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging.

Certain additional advantages and features of this invention may be apparent to those skilled in the art upon studying the disclosure, or may be experienced by persons employing the novel system and method of the present invention, chief of which is UV disinfection of ultrasound systems and methods of operation thereof are provided. Another advantage of the present systems and method is that conventional medical image systems may be upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A system comprising:
    a display;
    a control panel;
    an ultraviolet (UV) light source coupled to the display, wherein the UV light source is configured to turn on responsive to a control signal;
    an articulation system coupled to the display and configured to position the display; and
    a controller coupled to the UV light source and comprising a processor and a memory having encoded thereon a program of instruction, the processor executing the program of instruction to
    provide the control signal to turn on the UV light source responsive to the display being positioned in a disinfect position defined by articulation of the display, and
    prevent the UV light source from illuminating or turn off the UV light source responsive to a detection of an object between the control panel and the display while the display is in the disinfect position.

2. The system of claim 1 further comprising a position sensor coupled to the controller, wherein the position sensor is configured to provide to the controller position information of the display.

3. The system of claim 1, wherein the disinfect position is parallel to the control panel and over the control panel.

4. The system of claim 1, further comprising a motion sensor coupled to the controller, wherein the motion sensor is configured to detect a motion of the object between the control panel and the display, and wherein the controller is configured to provide a control signal to turn off the UV light source when the motion sensor detects the motion.

5. The system of claim 1, further comprising a touch sensor coupled to the controller, wherein the touch sensor is configured to detect a touch on the control panel, and wherein the controller is configured to provide a control signal to turn off the UV light source when the touch sensor detects the touch.

6. The system of claim 1, further comprising a timer coupled to the controller, wherein the timer is configured to set a length of a disinfection cycle, and wherein the controller is further configured to provide a control signal to turn off the UV light source upon completion of the disinfection cycle absent the detection of an object between the control panel and the display prior to the completion of the disinfection cycle.

7. The system of claim 1, wherein the controller is further configured to provide a graphic to the display.

8. The system of claim 7, wherein the controller is further configured to provide a disinfection status indicative of whether or not a disinfection has been interrupted to the display, wherein the graphic provided to the display is based, at least in part, on the disinfection status.

9. The system of claim 1, further comprising a second UV light source on the control panel.

10. The system of claim 1, wherein the UV light source is an LED.

11. The system of claim 1, further comprising an instrument holder adjacent to the control panel, wherein the instrument holder includes a second UV light source configured to illuminate an interior of the instrument holder.

12. The system of claim 1, wherein the control panel comprises:
a keyboard;
a track ball integrated with the keyboard; and
a second UV light source under the keyboard, the second UV light source configured to illuminate the track ball.

13. The system of claim 1, wherein the UV light source is one of a plurality of UV light sources arranged around a perimeter of the display.

14. The system of claim 1, wherein the UV light source is one of a plurality of UV light sources embedded within a screen portion of the display.

15. The system of claim 7, wherein the controller is configured to display the graphic until the user touches the control panel or begins an exam.

16. The system of claim 6, wherein the controller is further configured to provide a graphic to the display, the graphic indicating whether the UV light source was turned off before the disinfecting cycle was completed.

* * * * *